(12) United States Patent
Sorensen et al.

(10) Patent No.: US 7,897,186 B2
(45) Date of Patent: Mar. 1, 2011

(54) MODIFIED WHEY PROTEIN COMPOSITIONS HAVING IMPROVED FOAMING PROPERTIES

(75) Inventors: Thomas Sorensen, Raleigh, NC (US); Myke Rich, Knightdale, NC (US)

(73) Assignee: Novozymes North America, Inc., Franklinton, NC (US)

( * ) Notice: Subject to any disclaimer, the term of this patent is extended or adjusted under 35 U.S.C. 154(b) by 179 days.

(21) Appl. No.: 10/287,134

(22) Filed: Nov. 4, 2002

(65) Prior Publication Data

US 2003/0124647 A1 Jul. 3, 2003

Related U.S. Application Data

(60) Provisional application No. 60/333,215, filed on Nov. 6, 2001.

(51) Int. Cl.
*A23C 21/00* (2006.01)
(52) U.S. Cl. .............. 426/41; 426/34; 426/564; 426/583
(58) Field of Classification Search .......... 426/34, 426/35, 41, 42, 564, 580, 583
See application file for complete search history.

(56) References Cited

U.S. PATENT DOCUMENTS

| | | | |
|---|---|---|---|
| 3,935,323 A | 1/1976 | Feminella et al. | |
| 3,944,680 A | 3/1976 | Van Pelt et al. | |
| 4,029,825 A | 6/1977 | Chang | |
| 4,034,124 A | 7/1977 | Van Dam | |
| 4,106,991 A | 8/1978 | Markussen et al. | |
| 4,572,837 A | 2/1986 | Poole et al. | |
| 4,650,690 A | 3/1987 | Bams et al. | |
| 4,847,096 A | 7/1989 | Mellqvist et al. | |
| 4,861,610 A | 8/1989 | Kato et al. | |
| 5,028,447 A | 7/1991 | Schenk | |
| 5,079,028 A | 1/1992 | Wieske et al. | |
| 5,082,674 A * | 1/1992 | Carrell et al. | 426/52 |
| 5,543,169 A | 8/1996 | Colarow et al. | |
| 5,580,491 A | 12/1996 | Phillips et al. | |
| 5,681,505 A | 10/1997 | Phillips et al. | |
| 5,866,357 A | 2/1999 | Dambmann et al. | |
| 6,001,640 A | 12/1999 | Loeffler et al. | |
| 6,248,388 B1 | 6/2001 | Van Eedenburg et al. | |
| 6,399,121 B1 * | 6/2002 | Nielsen | 426/37 |

FOREIGN PATENT DOCUMENTS

| | | |
|---|---|---|
| CA | 2324922 | 2/2001 |
| EP | 426211 | 5/1991 |
| EP | 0 631 731 | 1/1995 |
| EP | 0 737 425 | 10/1996 |
| EP | 0 966 887 | 12/1999 |
| WO | WO 92/21247 | 12/1992 |
| WO | WO 00/42863 | 7/2000 |
| WO | WO 00/54601 | 9/2000 |
| WO | WO 01/06867 | 2/2001 |
| WO | WO 01/08502 | 2/2001 |
| WO | WO 02/13620 | 2/2002 |

OTHER PUBLICATIONS

Blecker et al, Modification of the Interfacial Properties of Whey by Enzymatic Hydrolysis of the Residual Fat, p. 85-89 (1995).

* cited by examiner

*Primary Examiner*—Leslie Wong
(74) *Attorney, Agent, or Firm*—Kristin J. McNamara

(57) ABSTRACT

Methods for improving the foaming properties of whey protein preparations by contacting an aqueous solution containing whey protein with a phospholipase are disclosed. Treatment of a whey protein preparation with a phospholipase results in a whey protein preparation having improved foam overrun and foam stability when whipped, as compared to a whey protein preparation that is not treated with a phospholipase.

26 Claims, 2 Drawing Sheets

MODIFIED WHEY PROTEIN COMPOSITIONS HAVING IMPROVED FOAMING PROPERTIES

CROSS-REFERENCE TO RELATED APPLICATIONS

This application claims the benefit of U.S. Provisional Application Serial No. 60/333,215, filed Nov. 6, 2001, the contents of which are hereby incorporated by reference.

FIELD OF THE INVENTION

The present invention relates to methods for modifying whey proteins and modified whey protein compositions having improved foaming properties.

BACKGROUND OF THE INVENTION

Whey is a by-product of the production of cheese. Traditionally, whey is disposed of as unused waste or used as fertilizer or animal feed. As an alternative to egg white solids, the food processing industry utilizes whey protein preparations to impart specific properties to a variety of formulated food products. For the food processing industry, whey protein represents an important and valuable source of ingredients due to its organoleptic properties and functional properties, as well as its lower cost compared to egg white solids.

One of the beneficial uses for whey protein in the food processing industry is as a foam. Whey proteins can be whipped to form a foam for use in, for example, low-calorie desserts, ice cream, and confectionary products. Unfortunately, whey protein tends to exhibit poor foaming properties as compared to egg white solids, including, poorer whippability and, after being whipped, poorer foam stability.

Many processes have been proposed to improve the foaming properties of whey protein. Phillips et al., U.S. Pat. No. 5,580,491, for example, describes non-enzymatic methods for modifying whey proteins to improve the foaming properties of the whey protein. Blecker et al., "Modification of the interfacial properties of whey by enzymatic hydrolysis of the residual fat", Food Macromolecules and Colloids, edited by Dickinson and Lorient, pp. 85-89 (1995), describes an enzymatic method for modifying whey protein by enzymatic hydrolysis with a lipase. Chen, WO 01/06867, also describes an enzymatic process for improving foaming properties by modifying a whey protein preparation using a protease.

Despite these and other advances, there is still a need in the art for processes for improving the foaming properties and organoleptic properties of whey proteins preparations.

SUMMARY OF THE INVENTION

The present invention provides methods for improving the foaming properties of whey protein preparations. The modified whey protein preparations of the present invention are prepared by contacting an aqueous solution containing whey protein with a phospholipase. Treatment with a phospholipase results in a whey protein preparation having improved foam overrun and foam stability when whipped, as compared to a whey protein preparation, which is not treated with a phospholipase. Furthermore, treatment of the whey protein with a phospholipase does not impart an undesirable flavor to the modified whey protein preparations or foam products prepared from the modified whey protein preparations.

The invention further relates to the use of phospholipases in the manufacture of products made from whey protein ingredients, wherein the phospholipase treatment is conducted on the whey protein ingredient. The invention also relates to products prepared by any of the processes described herein.

DETAILED SPECIFICATION OF THE INVENTION

Figure 1:
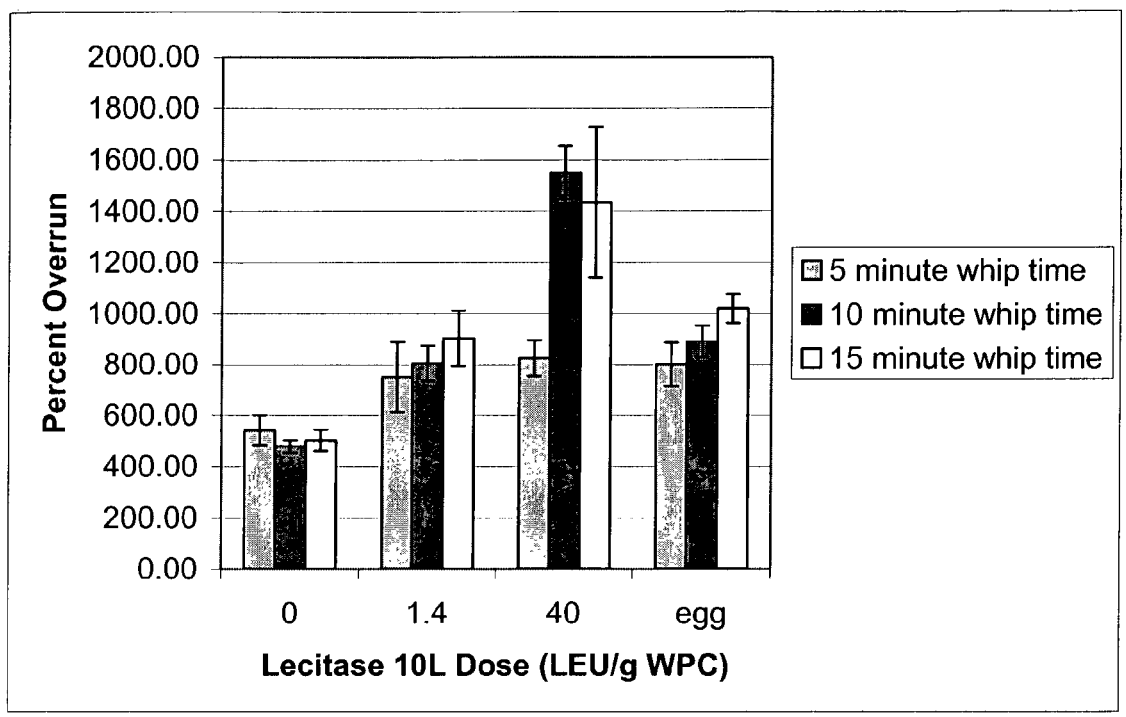
FIG. 1 is a graphic illustration of the effect of phospholipase treatment of whey protein concentrate on foam overrun.

Whey protein preparations having improved foaming properties when whipped may be prepared by contacting an aqueous solution containing whey protein with a phospholipase. The whey protein may be obtained by any method known in the art. Preferably, whey protein is obtained by one or more of ultrafiltration, electrodialysis, evaporation, and reverse osmosis of cheese whey. See, e.g., U.S. Pat. No. 3,547,900 and Horton et al., Food Technol., 26:30 (1972). Whey derived from any cheese source may be used, including cheddar cheese, Swiss cheese, mozzarella cheese and the like. Whey protein preparations, which typically contain beta-lactoglobulin and/or alpha-lactalbumin, are commercially available as whey protein concentrates (WPC) or whey protein isolates (WPI), from, e.g., Davisco (Le Sueur Minn.); Bio-Isolates PLC (Deeside, UK); NZMP North America (Santa Rosa Calif.); Formost Farms (Baraboo Wis.); MD Foods (Union N.J.); and Avenmore Waterford (Monroe Wis.). In a preferred embodiment, the whey protein is a whey protein concentrate.

As used in accordance with the present invention, the term "phospholipase" is intended to cover enzymes that have enzyme activity towards phospholipids as defined herein. Phospholipids consist of glycerol esterified with two fatty acids in an outer (sn-1) and the middle (sn-2) positions and esterified with phosphoric acid in the third position; the phosphoric acid, in turn, may be esterified to an amino-alcohol. Phospholipases are enzymes that participate in the hydrolysis of phospholipids. Several types of phospholipase activity can be distinguished, including phospholipases $A_1$ and $A_2$, which hydrolyze one fatty acyl group (in the sn-1 and sn-2 position, respectively) to form lysophospholipid; and lysophospholipase, and phospholipase B, which hydrolyzes the remaining fatty acyl group in lysophospholipid. The term phospholipase as used herein, includes, phospholipase $A_1$, phospholipase $A_2$ or phospholipase B, and combinations thereof.

The phospholipase treatment may be provided by one or more phospholipases, such as two or more phospholipases, including, without limitation, treatment with both type A and B; both type $A_1$ and $A_2$; both type $A_1$ and B; both type $A_2$ and B; or treatment with two different phospholipase of the same type. Also included is treatment of the whey protein with only one type of phospholipase, such as, $A_1$, $A_2$ or B. In a preferred embodiment of the invention, the phospholipase enzyme activity is provided by an enzyme having only phospholipase activity or essentially only phospholipase activity and wherein the phospholipase enzyme activity is not a side activity of the enzyme.

The phospholipase may be of any origin, e.g. of animal origin (such as, e.g. mammalian), e.g. from pancreas (e.g. bovine or porcine pancreas), or snake venom or bee venom. Alternatively, the phospholipase may be of microbial origin, e.g. from filamentous fungi, yeast or bacteria, such as the genus or species *Aspergillus*, e.g. *A. niger; Dictyostelium*, e.g. *D. discoideum; Mucor*, e.g. *M. javanicus, M. mucedo, M. subtilissimus; Neurospora*, e.g. *N. crassa; Rhizomucor*, e.g. *R. pusillus; Rhizopus*, e.g. *R. arrhizus, R. japonicus, R. stolonifer, Sclerotinia*, e.g. *S. libertiana; Trichophyton*, e.g. *T. rubrum; Whetzelinia*, e.g. *W. sclerotiorum; Bacillus*, e.g. *B. megaterium, B. subtilis; Citrobacter*, e.g. *C. freundii; Enterobacter*, e.g. *E. aerogenes, E. cloacae Edwardsiella, E. tarda; Erwinia*, e.g. *E. herbicola; Escherichia*, e.g. *E. coli; Klebsiella*, e.g. *K. pneumoniae; Proteus*, e.g. *P. vulgaris; Providencia*, e.g. *P. stuartii; Salmonella*, e.g. *S. typhimurium; Serratia*, e.g. *S. liquefasciens, S. marcescens; Shigella*, e.g. *S. flexneri; Streptomyces*, e.g. *S. violeceoruber, Yersinia*, e.g. *Y. enterocolitica*. Thus, the phospholipase may be fungal, e.g. from the class Pyrenomycetes, such as the genus *Fusarium*, such as a strain of *F. culmorum, F. heterosporum, F. solani*, or a strain of *F. oxysporum*. The phospholipase may also be from a filamentous fungus strain within the genus *Aspergillus*, such as a strain of *Aspergillus awamori, Aspergillus foetidus, Aspergillus japonicus, Aspergillus niger* or *Aspergillus oryzae*. A preferred phospholipase is derived from a strain of *Fusarium*, particularly *F. oxysporum*, e.g. from strain DSM 2627 as described in WO 98/26057, especially described in claim 36 and SEQ ID NO. 2 of WO 98/26057. In further embodiments, the phospholipase is a phospholipase as disclosed in PCT/DK/00664.

The phospholipase used in the process of the invention may be derived or obtained from any of the sources mentioned herein. The term "derived" means in this context that the enzyme may have been isolated from an organism where it is present natively, i.e. the identity of the amino acid sequence of the enzyme are identical to a native enzyme. The term "derived" also means that the enzymes may have been produced recombinantly in a host organism, the recombinant produced enzyme having either an identity identical to a native enzyme or having a modified amino acid sequence, e.g. having one or more amino acids which are deleted, inserted and/or substituted, i.e. a recombinantly produced enzyme which is a mutant and/or a fragment of a native amino acid sequence or an enzyme produced by nucleic acid shuffling processes known in the art. Within the meaning of a native enzyme are included natural variants. Furthermore, the term "derived" includes enzymes produced synthetically by e.g. peptide synthesis. The term "derived" also encompasses enzymes which have been modified e.g. by glycosylation, phosphorylation etc., whether in vivo or in vitro. The term "obtained" in this context means that the enzyme has an amino acid sequence identical to a native enzyme. The term encompasses an enzyme that has been isolated from an organism where it is present natively, or one in which it has been expressed recombinantly in the same type of organism or another, or enzymes produced synthetically by e.g. peptide synthesis. With respect to recombinantly produced enzyme the terms "obtainable" and "derived" refers to the identity of the enzyme and not the identity of the host organism in which it is produced recombinantly.

The phospholipase may be obtained from a microorganism by use of any suitable technique. For instance, a phospholipase enzyme preparation may be obtained by fermentation of a suitable microorganism and subsequent isolation of a phospholipase preparation from the resulting fermented broth or microorganism by methods known in the art. The phospholipase may also be obtained by use of recombinant DNA techniques. Such method normally comprises cultivation of a host cell transformed with a recombinant DNA vector comprising a DNA sequence encoding the phospholipase in question and the DNA sequence being operationally linked with an appropriate expression signal such that it is capable of expressing the phospholipase in a culture medium under conditions permitting the expression of the enzyme and recovering the enzyme from the culture. The DNA sequence may also be incorporated into the genome of the host cell. The DNA sequence may be of genomic, cDNA or synthetic origin or any combinations of these, and may be isolated or synthesized in accordance with methods known in the art.

Suitable phospholipases are available commercially. In a preferred embodiment, the phospholipase is a pancreas-derived phospholipase A2, such as Lecitase® (Novozymes North America, Inc.).

The phospholipase may also be a purified phospholipase. The term "purified" as used herein covers phospholipase enzyme protein free from components from the organism from which it is derived. The term "purified" also covers phospholipase enzyme protein free from components from the native organism from which it is obtained, this is also termed "essentially pure" phospholipase and may be particularly relevant for phospholipases which are naturally occurring phospholipases and which have not been modified genetically, such as by deletion, substitution or insertion of one or more amino acid residues. The phospholipase may be purified, with only minor amounts of other proteins being present. The expression "other proteins" relate in particular to other enzymes. The term "purified" as used herein also refers to removal of other components, particularly other proteins and most particularly other enzymes present in the cell of origin of the phospholipase. The phospholipase may be "substantially pure", i.e. free from other components from the organism in which it is produced, i.e., e.g., a host organism for recombinantly produced phospholipase. Preferably, the enzymes are at least 75% (w/w) pure, more preferably at least 80%, at least 85%, at least 90%, at least 95%, at least 96%, at least 97%, at least 98%, or at least 99% pure. In another preferred embodiment, the phospholipase is 100% pure.

The term phospholipase also includes whatever auxiliary compounds that may be necessary for the enzyme's catalytic activity, such as, e.g. an appropriate acceptor or cofactor, which may or may not be naturally present in the reaction system.

The phospholipase may be in any form suited for the use in the treatment process, such as e.g. in the form of a dry powder or granulate, a non-dusting granulate, a liquid, a stabilized liquid, or a protected enzyme. Granulates may be produced, e.g. as disclosed in U.S. Pat. Nos. 4,106,991 and 4,661,452, and may optionally be coated by methods known in the art. Liquid enzyme preparations may, for instance, be stabilized by adding stabilizers such as a sugar, a sugar alcohol or another polyol, lactic acid or another organic acid according to established methods. Protected enzymes may be prepared according to the method disclosed in EP 238,216.

The enzymatic treatment in the process of the invention may be conducted by dispersing the phospholipase into an aqueous solution containing whey protein or admixing whey protein and a phospholipase in the presence of water, and allowing the enzyme reaction to take place at an appropriate holding-time and at an appropriate temperature. A reaction mixture is formed by adding to the aqueous whey protein-containing solution a phospholipase in an amount sufficient to improve the foaming properties of the whey protein preparation. The treatment with phospholipase may be carried out at conditions chosen to suit the selected enzymes according to principles well known in the art. It will be understood that each of the reaction conditions (such as, e.g., concentration of protein substrate, ratio of enzyme:substrate, pH, temperature, and time) may be varied, depending upon, e.g., the source of the whey protein substrate and/or enzyme. It will further be understood that optimization of the reaction conditions may be achieved using routine experimentation by establishing a matrix of conditions and testing different points in the matrix.

The phospholipase(s) is (are) added in an effective amount. The term "effective amount" means an amount sufficient to achieve the desired modification(s) described herein. In a preferred embodiment of the present invention, an aqueous solution is prepared containing a whey protein isolate or whey protein concentrate at a concentration corresponding to between 1% and 50% w/w protein, preferably about 5 to 40%, and most preferably about 10 to 20%. Preferably, the phospholipase is added in an amount of about 0.01 to 1.0% (w/w) on fat basis and more preferably in an amount of about 0.02 to 0.2% (w/w) on fat basis (assuming an enzyme product activity of 10,000 units/g). Preferably, the reaction mixture is incubated or reacted at a temperature of between about 25-55° C., more preferably between 40-50° C. Preferably, the reaction time is between about 10-120 minutes, more preferably between 10 and 60 minutes. The enzymatic treatment may be conducted at any suitable pH, such as e.g. in the range 5 to 9, more preferably at a pH of 6 to 8.

The enzymatic treatment may be conducted batchwise, e.g. in a tank with stirring, or it may be continuous, e.g. a series of stirred tank reactors, or by any suitable process known in the art.

Optionally, after the enzymatic treatment the phospholipase enzyme protein is removed/reduced and/or the enzyme is inactivated. Accordingly, in some embodiments, the methods of the invention encompass an additional step of inactivating or removing the phospholipase. Inactivation may be achieved by any method known in the art, including, without limitation, increasing the temperature of the reaction mixture to above about 70° C. and decreasing the pH of the reaction mixture to below about 5.0; increasing the pressure to above about 6000 bar; and any other method known in the art. Removal of the phospholipase may be achieved by, e.g., filtration or immobilization, including the use of immobilized enzymes. Inactivation or removal of the phospholipase is monitored by testing residual phospholipase activity, using any method known in the art.

In some embodiments, the methods of the invention encompass one or more additional steps of processing the modified whey protein by, e.g., drying, including spray-drying and freeze-drying; and concentrating, which can be achieved using, e.g., evaporation or membrane filtration.

The present invention provides modified whey protein preparations that exhibit improved foaming properties relative to unmodified whey protein preparations. Improved foaming can be measured as described in Example 2 below. Foaming overrun is defined as the weight of a given volume of solution minus the weight of the same volume of foam×100. An increased foaming capacity is defined as an increase in foaming overrun. Typically, the methods of the invention result in a foaming overrun of at least about 800%, preferably at least 1200% and most preferably at least 1500%, and an increased foaming capacity of at least 2-fold, preferably at least 5-fold, relative to that exhibited by the unmodified protein.

The present invention also provides modified whey protein preparations that exhibit improved stability relative to the unmodified protein preparations from which they are derived. Foam stability is measured as described in Phillips et al., *J. Food Sci.* 55, no. 4, 1991 and in Example 3 below, and is expressed the time required for half of the original weight of foam to drain as a liquid (50% drainage). In preferred embodiments, the modified whey protein preparations of the invention exhibit a foam stability of at least 10 min, more preferably at least 30 min, and most preferably at least 60 min.

In accordance with the present invention, the modified whey protein is able to be readily whipped into a stable foam, and can thus replace egg whites. The whey protein preparation can then be used as an ingredient in the manufacture of a variety of different food products that require a high-foaming and stable foam producing ingredient, including, without limitation, baked goods, such as cakes, whipped toppings, frostings, frozen yogurt, and mousse.

The present invention is illustrated by the following detailed examples, which are not intended to be limiting but merely exemplary of the scope of the present invention. Furthermore, all references previously mentioned are herein incorporated by reference.

EXAMPLES

Example 1

Freeze Dried Whey Protein Concentrate

Whey protein concentrate (WPC) (80% dry basis soluble WPC, Leprino Foods) containing 78% protein was used to make 10% protein solutions. One solution was left as a control (no phospholipase added), one solution was treated with 1.4 LEU Lecitase 10 L/g WPC (Novozymes North America, Inc.), and the last solution was treated with 40 LEU Lecitase 10 L/g WPC. All three solutions were heated to 50° C. for 30 minutes, allowed to cool to room temperature, and frozen overnight. Once frozen the samples were freeze dried until becoming a fine powder.

Example 2

Foam Formation and Overrun Measurements

Overrun measurements were made at 5 minute intervals for a total of 15 minutes whipping using 150 mL of 5% dispersions of the above mentioned untreated and treated freeze-dried whey protein concentrates. The dispersions were adjusted to pH 7.00.

Five percent freeze-dried whey protein concentrate (FD-WPC) dispersions from Example 1 and 5% egg white protein powder (untreated) (Ballas Egg Products, 81.83% protein determined by LECO) dispersions were whipped with a double beater Sunbeam Mastermixer 275 Watts. The Master-mixer was used at a speed of 11, which according to the manufacturer is the optimum setting for egg white foams. The protein dispersion (150 mL) was poured into the stainless steel bowl and whipped for 5-minute intervals. After each 5-minute interval the mixer was stopped and the mixer head was carefully removed to minimize foam destruction. Samples of foam were gently scooped out with a spatula and placed in two pre-weighted boats that were be quickly filled with foam using small scoops and avoiding large air pockets. A spatula was used to level the top of the foam even with the weighing boat to obtain constant volume in each measurement. The weight was recorded and the foam was then returned to the bowl and whipping resumed.

$$\% \text{ Overrun} = \frac{(\text{wt } 100 \text{ mL protein}) - (\text{wt } 100 \text{ mL foam})}{(\text{wt } 100 \text{ mL foam})} \times 100$$

The overrun profiles offer insight into the overall protein interactions involved in film formation during foam formation (Phillips et al 1987) while drainage indicates the overall stability of the foam. Treatment of WPC with Lecitase 10L increased percent overrun substantially when compared to the untreated WPC (FIG. 1). When dosed at 1.4 LEU Lecitase 10 L/g WPC the overrun measurement is almost equal to the overrun measurement of egg white protein.

Example 3

Foam Stability Measurements

Foam stability measurements were made for a total of 15 minutes whipping using 150 mL of 5% dispersion of the above mentioned untreated and treated FDWPC. The dispersions were adjusted to pH 7.00.

To measure foam stability, i.e. drainage, the whipping bowl was modified by drilling a hole in the bowl. A piece of tape was placed over the hole until measurement of drainage began. The protein dispersion was poured into the bowl. The bowl, beaters and protein dispersion were weighed and then whipping was started at speed 11 for 15 minutes. A timer was started when whipping was completed. The bowl, beaters and foam were weighed to quantify moisture lost during whipping. The tape was then removed from the bowl and a pre-weighed weigh boat was placed under the hole. Weight of drained fluid was taken every 5 minutes and the time to 50% drainage was reported.

Figure 2:
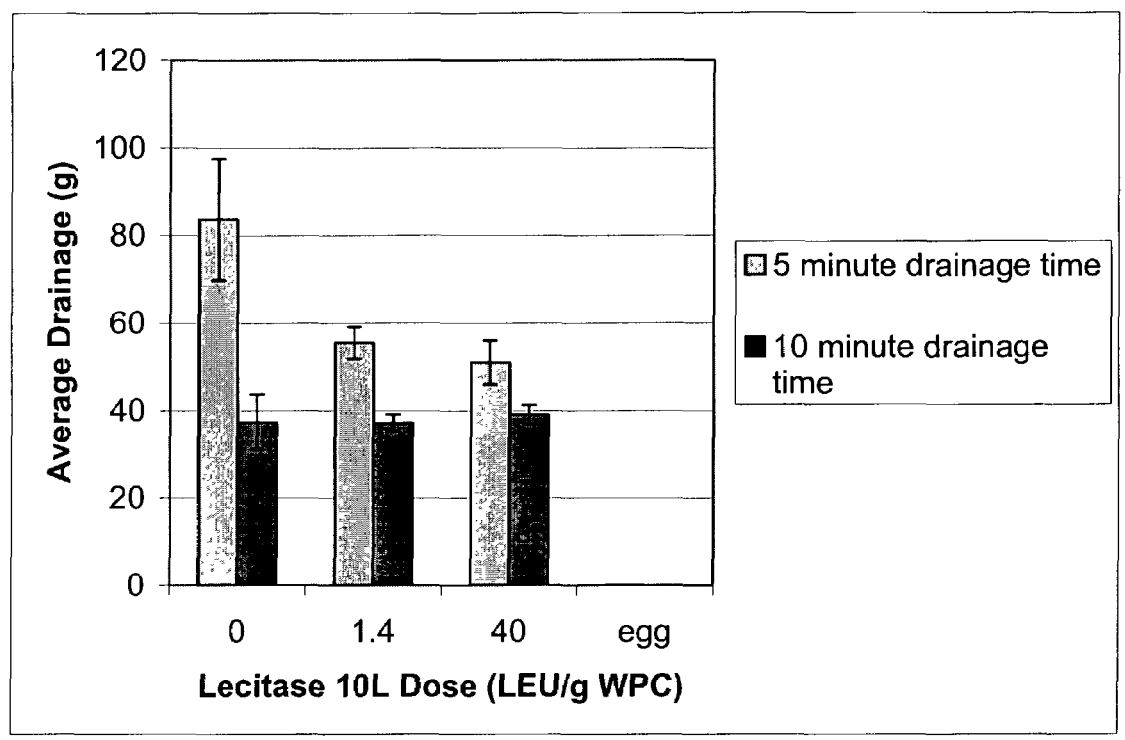
FIG. 2 is a graphic illustration of the effect of phospholipase treatment of whey protein concentrate on foam stability, measured by drainage time.

Stability measurements are also increased with treatment using Lecitase 10L. When compared to the untreated FDWPC foam sample, average drainage in the first 5 minutes decreased (FIG. 2). The average drainage in the second five minutes was about equal in the untreated and treated samples. This shows that treatment of the protein did decrease the overall weight drained in 10 minutes. The increased stability did not hold firm when compared to egg white protein foams. The egg white foams showed negligible drainage in the first 10 minutes of observation and drained 50% of total solution only after 45 minutes. Though the FDWPC foams treated with Lecitase 10L are not as stable as egg white foams, they are more stable than the controls. Thus, treatment of WPC with Lecitase 10L improved foam overrun and foam stability when compared to untreated WPC.

Example 4

Protein Determination Using the LECO

Percent nitrogen was determined on FDWPC samples using the LECO. Percent protein was calculated by multiplying the percent nitrogen by 6.38.

Example 5

Moisture Determination Using the CEM

Moisture was determined on FDWPC samples using 80% power with a time interval of 15 seconds and a differential weight of 0.2 mg.

Example 6

Fat Determination Using the Babcock Method

Fat was determined on 20% FDWPC samples (20 g WPC in 100 g total solution). Procedure followed from EUS-SM-0204 Determination of Fat in Dairy Products by Babcock Methods.

Table I shows the compositional analysis for both sets of FDWPC when treated with Lecitase 10L. Percent protein, percent moisture, and percent fat of the four samples were similar in value, especially percent fat values. All solutions made using the FDWPC were adjusted on a percent protein (w/w) basis. So protein and fat were kept constant throughout the experiments.

TABLE I

Compositional analysis of FDWPC

| Sample | Percent Protein | Percent Moisture | Percent Fat | Total |
|---|---|---|---|---|
| Untreated FDWPC (1) | 84.2 | 0.16 | 0.1 | 84.46 |
| 40 LEU Lecitase 10 L/g WPC FDWPC (1) | 84.2 | 0.16 | 0.1 | 84.46 |
| Untreated FDWPC (2) | 81.9 | 0.20 | 0.1 | 82.10 |
| 1.4 LEU Lecitase 10 L/g WPC FDWPC (2) | 83.3 | 0.18 | 0.1 | 83.58 |

The invention claimed is:

1. A method for producing a foam product from a protein comprising:
   (a) adding one or more phospholipases to an aqueous solution of a whey protein concentrate or a whey protein isolate to form a reaction mixture;
   (b) incubating the reaction mixture to produce a modified whey protein preparation; and
   (c) whipping the modified whey protein preparation into a foam which has improved foam overrun and foam stability compared to a whey protein concentrate or a whey protein isolate which has not been treated with the one or more phospholipases.

2. The method of claim 1, which comprises dispersing the phospholipase into an aqueous solution comprising the whey protein preparation.

3. The method of claim 1, wherein the one or more phospholipases are purified phospholipases.

4. The method of claim 1, wherein the one or more phospholipases are a phospholipase A.

5. The method of claim 1, wherein the one or more phospholipases are a phospholipase A1.

6. The method of claim 1, wherein the one or more phospholipases are a phospholipase A2.

7. The method of claim 1, wherein the one or more phospholipases are a phospholipase B.

8. The method of claim 1, wherein the one or more phospholipases are a combination of phospholipase A1 and A2.

9. The method of claim 1, wherein the one or more phospholipases are a combination of phospholipase A and phospholipase B.

10. The method of claim 1, wherein the one or more phospholipases are selected from the group consisting of phospholipase A1, phospholipase A2, phospholipase B and any combination thereof.

11. The method of claim 1, wherein the one or more phospholipases are added to the aqueous solution in an amount of 0.01 to 1% (w/w) on fat basis.

12. The method of claim 1, wherein the modified whey protein preparation exhibits a foam stability of at least 10 minutes.

13. The method of claim 1, wherein the modified whey protein preparation exhibits a foam stability of at least 30 minutes.

14. The method of claim 1, wherein the modified whey protein preparation exhibits a foam stability of at least 60 minutes.

15. The method of claim 1, wherein the modified whey protein preparation has a foaming overrun of at least 800%.

16. The method of claim 1, wherein the modified whey protein preparation has a foaming overrun of at least 1200%.

17. The method of claim 1, wherein the modified whey protein preparation has a foaming overrun of at least 1500%.

18. The method of claim 1, wherein the modified whey protein preparation has a foaming capacity which is at least two times greater than the foaming capacity of the whey protein preparation which has not been treated with the one or more phospholipases.

19. The method of claim 1, wherein the modified whey protein preparation has a foaming capacity which is at least five times greater than the foaming capacity of the whey protein preparation which has not been treated with the one or more phospholipases.

20. The method of claim 1, further comprising, subsequent to step c), inactivating the phospholipase enzyme.

21. The method of claim 1, further comprising drying the modified whey protein preparation.

22. The method of claim 1, further comprising concentrating the modified whey protein preparation.

23. The method of claim 1, wherein the reaction mixture is incubated for 10-120 minutes.

24. The method of claim 1, wherein the reaction mixture is incubated at a temperature of 25-550° C.

25. The method of claim 1, wherein the reaction mixture is incubated at a pH of 5-9.

26. The method of claim 1, wherein the whey protein concentrate is in the form of a freeze-dried whey protein concentrate.

* * * * *